(12) United States Patent
Han et al.

(10) Patent No.: US 6,477,898 B1
(45) Date of Patent: Nov. 12, 2002

(54) MEMBRANE MASK STRESS MEASUREMENT APPARATUS AND METHOD THEREFOR

(75) Inventors: Sang-In Han, Phoenix, AZ (US); Pawitter Mangat, Gilbert, AZ (US)

(73) Assignee: Motorola, Inc., Schaumburg, IL (US)

( * ) Notice: Subject to any disclaimer, the term of this patent is extended or adjusted under 35 U.S.C. 154(b) by 299 days.

(21) Appl. No.: 09/610,501

(22) Filed: Jul. 6, 2000

(51) Int. Cl.[7] ............................................. G01N 29/06
(52) U.S. Cl. .............................. 73/579; 73/596; 73/643; 73/659
(58) Field of Search ........................... 73/657, 579, 659, 73/643, 12.01, 596

(56) References Cited

U.S. PATENT DOCUMENTS

| | | | |
|---|---|---|---|
| 3,726,129 A | * 4/1973 | Thorne | 73/67.2 |
| 3,958,450 A | * 5/1976 | Klesattel | 73/67.2 |
| 4,283,952 A | * 8/1981 | Newman | 73/598 |
| 4,342,907 A | * 8/1982 | Macedo et al. | 73/705 |
| 5,804,698 A | * 9/1998 | Belonenko et al. | 73/1.83 |
| 6,006,594 A | * 12/1999 | Karrai et al. | 73/105 |
| 6,068,597 A | * 5/2000 | Lin | 600/443 |
| 6,200,022 B1 | * 3/2001 | Hammiche et al. | 374/46 |
| 6,257,053 B1 | * 7/2001 | Tomita et al. | 73/105 |
| 6,318,159 B1 | * 11/2001 | Chen et al. | 73/105 |

OTHER PUBLICATIONS

Michael P. Schlax et al., "Stress mapping techniques for the SCALPEL mask membrane system", 1999 SPIE Symposium on Emerging Lithographic Tech., vol. 3676, pp. 152–161, 1999.

M.P. Schlax et al., "Thin film stress mapping using an integrated sensor", J. Vac. Sci. Technologies, B 17(6), Nov./Dec. 1999, pp. 2714–2718.

* cited by examiner

Primary Examiner—Hezron Williams
Assistant Examiner—Jacques Saint-Surin
(74) Attorney, Agent, or Firm—James L. Clingan, Jr.

(57) ABSTRACT

A method and apparatus for determining stress levels of membrane masks that may be used in membrane-based lithographic techniques is presented. A piezoelectric plate (30) is used to induce vibrations into the membrane mask (35), where the frequency and amplitude of the vibrations induced in the membrane layer (50) are optically sensed. By comparing the stimulus applied to the piezoelectric plate (30) with the response sensed optically in a gain phase analyzer (80), a frequency graph (110) associated with the membrane layer (50) is constructed such that resonant frequencies are easily determined. These resonant frequencies can then be used to calculate the stress associated with the membrane layer (50).

34 Claims, 2 Drawing Sheets

MEMBRANE MASK STRESS MEASUREMENT APPARATUS AND METHOD THEREFOR

FIELD OF THE INVENTION

The invention relates generally to integrated circuit manufacturing and more particularly to a membrane mask stress measurement apparatus and method therefor.

RELATED ART

As semiconductor device geometries continue to decrease, more advanced lithographic techniques are required to achieve the patterning required to support such geometries. Some examples include x-ray lithography (XRL), ion beam projection lithography (IPL), extreme ultra-violet (EUV) lithography, and scattering with angular limited projection in electron-beam lithography (SCALPEL). SCALPEL, IPL and x-ray lithography techniques utilize masks that are formed of attenuating elements overlying thin membranes. The membrane thickness of a SCALPEL mask is typically in the range of 100–150 nanometers, whereas for XRL and IPL the membrane thickness is typically in the range of 2–5 microns. In order to fabricate the membrane mask, the silicon substrate is etched away to create free-standing membranes. SCALPEL masks typically include 500 to 1000 thin membrane windows approximately 1 mm×12 mm in size on a 200 mm silicon starting substrate. In contrast, XRL and IPL masks consist of one large membrane window on a silicon substrate.

SCALPEL membrane masks can suffer from distortions created through local stress on the membrane. As such, when various layers that may be included in the membrane mask are deposited, the deposition parameters may vary slightly from the ideal parameter settings such that the stress of one layer may not exactly match the expected stress of another layer. This mismatch may cause undesirable stress levels when composite layer membrane masks are formed where significant stress mismatch exists between various layers included in the composite layer structure.

In order to optimize the image placement requirements of the SCALPEL lithographic technique, the stress associated with a particular membrane mask used in the lithographic operations must be determined to lie within predetermined specification levels. By understanding what the stress level is for the membrane mask, the appropriate process alterations can be made to ensure minimal image placement deviations.

One technique used for measuring stress of thin films on substrates such as silicon wafers is a bow measurement test that measures the curvature of the substrate by reflecting light off the substrate after film deposition. The curvature of the substrate before and after deposition of the thin films is compared to determine the stress induced by the deposition of the thin films. Although such techniques work well for films having a thickness on the same order as the thickness of the underlying substrate, such techniques do not work well when the film thickness is orders of magnitude smaller than the substrate thickness. This is because the stress associated with the thick substrate renders the stress added by the thin films insignificant.

In order to avoid rendering the stress associated with the thin films insignificant, membranes made up of thin films alone may be fabricated for stress testing. One technique which utilizes such thin film membranes is bulge testing. In bulge testing, the membrane is suspended between two different pressures. The stress of the membrane can then be measured based on the "bulging" or distortion of the membrane resulting from the pressure differential.

In applications that include thin film membranes, such as SCALPEL masks, more accurate methods of stress measurement are required to ensure accurate lithographic results. One technique that has been used for measuring stress levels for SCALPEL membrane masks is based on a resonant frequency test (RFT). The RFT technique measures the stress of the free-standing membrane by inducing vibrations within the membrane under test. Such vibration inducement is accomplished in one prior art RFT technique through the use of electrostatic force. The electrostatic force is generated by applying a sinusoidal voltage to an underlying conductive chuck structure that drives the overlying membrane as well as physically supporting it. The chuck includes an array of complementary driving electrodes that correspond to the locations of membrane widows within the membrane mask. Each driving electrode stimulates a corresponding membrane widow.

A sensing electrode positioned over the membrane under test measures the voltage change generated between the electrode and the vibrating membrane. This is a capacitance-based measurement. At each membrane window test site, the voltage and frequency of the input signal applied to the drive electrodes included in the underlying chuck is manually adjusted while the output is observed on an oscilloscope or similar testing apparatus. When the amplitude of the vibrations reaches a peak level (which can be determined based on the output signal on the oscilloscope), a resonant frequency of the membrane under test is determined. The resonant frequency is then used in the following formula to determine the stress (in MPa) within the membrane.

$$\text{Stress} = (4 f_r^2 \rho) / [(m/a)^2 + (n/b)^2]$$

In the formula, $f_r$ is the resonance frequency of the membrane, $\rho$ is the average film density in g/cm$^3$, a and b are the rectangular edge length and width of the membrane widow in centimeters, and m and n are the number of halfwaves in the a and b directions, respectively. Membrane vibrations are detected using a capacitive measurement that senses a change in capacitance that results from the changing distance between the sensing electrode and the vibrating membrane. This particular RFT technique suffers from a number of disadvantages that may limit its effectiveness in testing membrane masks.

One fundamental problem associated with this prior art RFT technique is the low throughput in measurement. Since the capacitive sensor mounted on the micrometer is positioned inside the vacuum chamber, repositioning of the sensor to another membrane window and tuning the gap between the sensor and membrane using the micrometer requires breaking the vacuum. As a result, a considerable amount of time is required for measuring hundreds of membrane windows included on a mask. Although the time required can be reduced by installing an x-y stage mounted on a guide rail inside the vacuum chamber, this adds complexity to the measurement system as a servo motor control is required. Furthermore, the manual control in sweeping frequency around the resonance frequency and visual inspection of peak amplitude of the output signal is also time consuming.

Another drawback of prior art RFT technique is the measurement inaccuracy. Since the resonance peak is determined by visual inspection of peak amplitude of voltage, choosing the peak amplitude becomes arbitrary when the Q factor (energy storing efficiency factor) is not high, which is the case for thin membranes included in SCALPEL masks. Determination of the peak amplitude can also be problematic due to the presence of noise in the detected signal. This noise is further aggravated when the driving signal can be fed-through to the detected signal by capacitive coupling.

Furthermore, RFT measurement techniques based on the capacitive excitation cannot measure the resonance frequency of a membrane that does not have a conductive layer. In order to cause the membrane to vibrate due to electrostatic excitation, the membrane must include a conductive layer such that a ground plane is created to allow for the electrostatic excitation. This may be undesirable in some membrane structures where a conductive layer is not present or needed for lithographic purposes. For example, in one instance a single layer membrane may be measured for its stress level, such that this stress level can be compared with the stress level measured after an additional layer has been added to the initially measured layer.

Prior art RFT techniques are also limited by the need for a custom chuck that includes the drive electrodes for each substrate size and each pattern of membrane windows included on a mask. Thus, for different size masks or masks of the same size that have different window formats, a different chuck with specifically placed and sized drive electrodes will be required in order to achieve the electrostatic excitation desired. Furthermore, due to the fact that the electrostatic excitation and sensing associated with the prior art technique is generally inefficient in terms of driving and sensing, higher excitation voltages are typically required. These higher excitation voltages may cause a distortion or shifting of the frequency spectrum around the resonant frequency, which is undesirable.

Therefore, prior art RFT techniques do not provide the level of accuracy desired, nor do they provide the high throughput necessary for use in manufacturing environments.

BRIEF DESCRIPTION OF THE DRAWINGS

The present invention is illustrated by way of example and not limitation in the accompanying figures, in which like references indicate similar elements, and in which.

Skilled artisans appreciate that elements in the figures are illustrated for simplicity and clarity and have not necessarily been drawn to scale. For example, the dimensions of some of the elements in the figures may be exaggerated relative to other elements to help improve the understanding of the embodiments of the present invention.

DETAILED DESCRIPTION

Generally, the present invention provides a method and apparatus for determining stress levels of membrane masks that may be used in membrane-based lithographic techniques. A piezoelectric plate is used to induce vibrations into the membrane mask, where the gain and phase changes that depend on the frequency of vibrations induced in the membrane mask are optically sensed. By comparing the stimulus applied to the piezoelectric plate with the response sensed optically in a gain phase analyzer, a frequency graph associated with the membrane mask can be constructed such that resonant frequencies are easily determined. These resonant frequencies can then be used to calculate the stress associated with the membrane mask.

The piezoelectric plate can provide adequate excitation of the membrane mask using low excitation voltages such that undesirable distortions associated with high excitation voltages are avoided. The noise that existed in prior art RFT techniques is also avoided by utilizing optical sensing to measure the vibrations of the membrane mask. By enclosing the membrane mask in a vacuum environment with a transparent cover, the optical measurement apparatus associated with measuring the frequency response of each membrane window is easily shifted from one membrane window to the next without having to remove the membrane mask from the vacuum environment. As such, the throughput associated with testing membrane masks that include a large number of membrane windows is greatly improved over that of prior art RFT techniques. The ease with which the resonant frequency is determined based on the frequency graph provided by the gain phase analyzer simplifies the actual measurement techniques and further improves the expected throughput. Thus, manual interaction with the testing system is minimized, which further increases testing efficiency.

Figure 1:
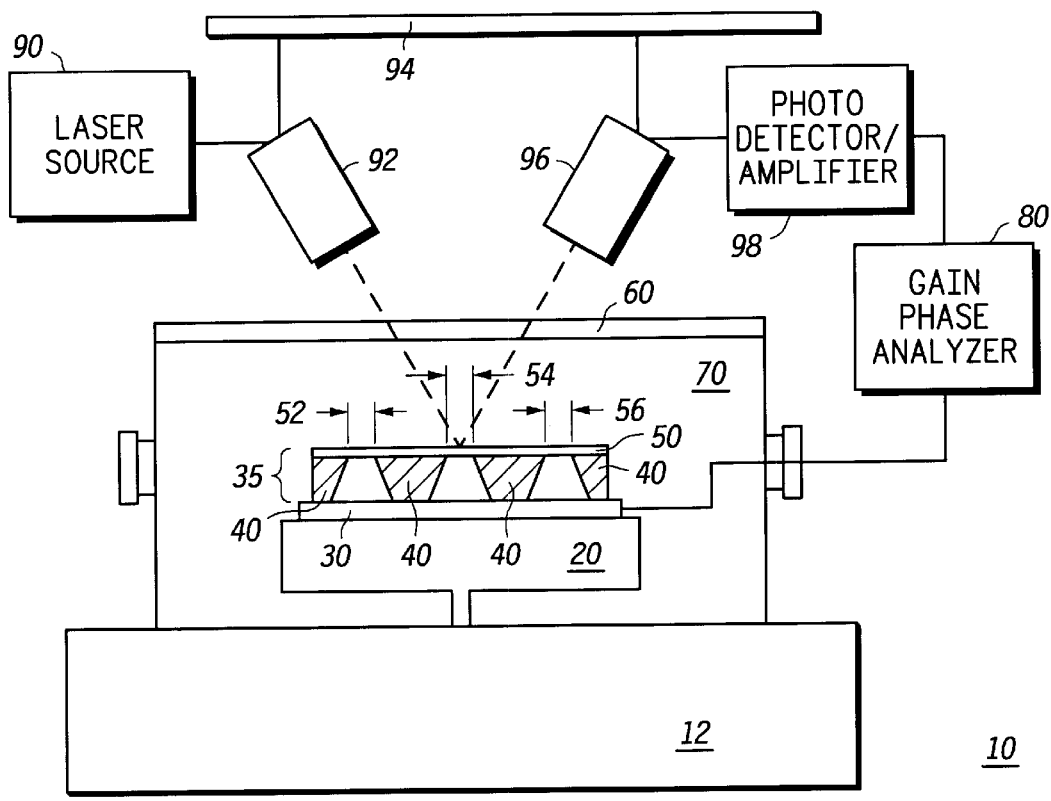
FIG. 1 includes a graphical representation of a stress measurement apparatus in accordance with a particular embodiment of the present invention.
Figure 2:
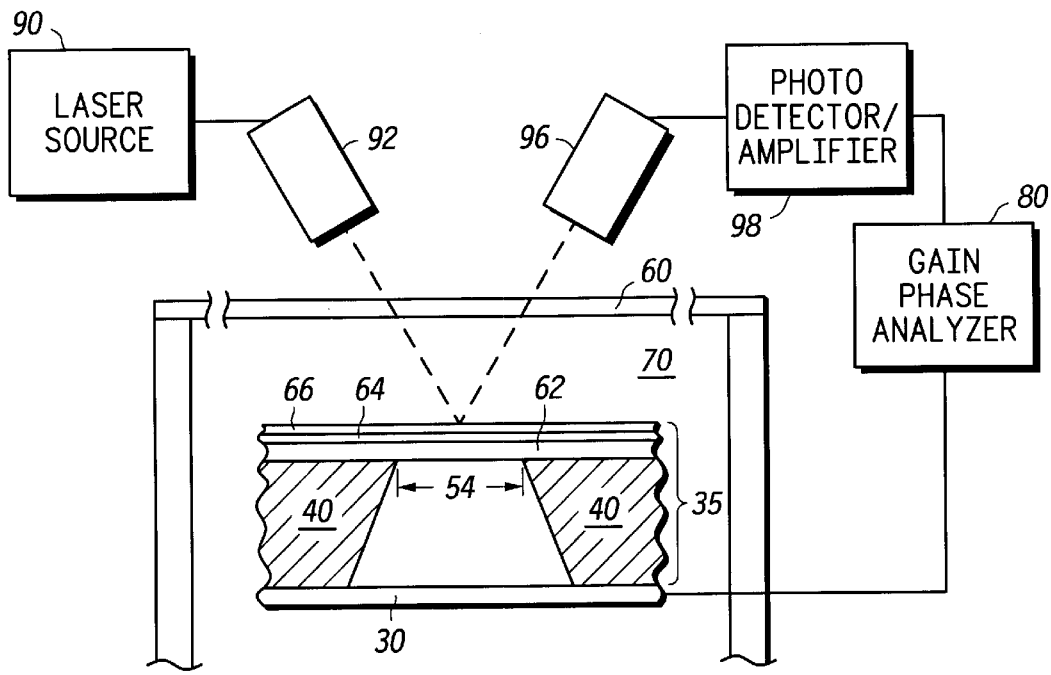
FIG. 2 includes a magnified view of the membrane under test shown in FIG. 1.
Figure 3:
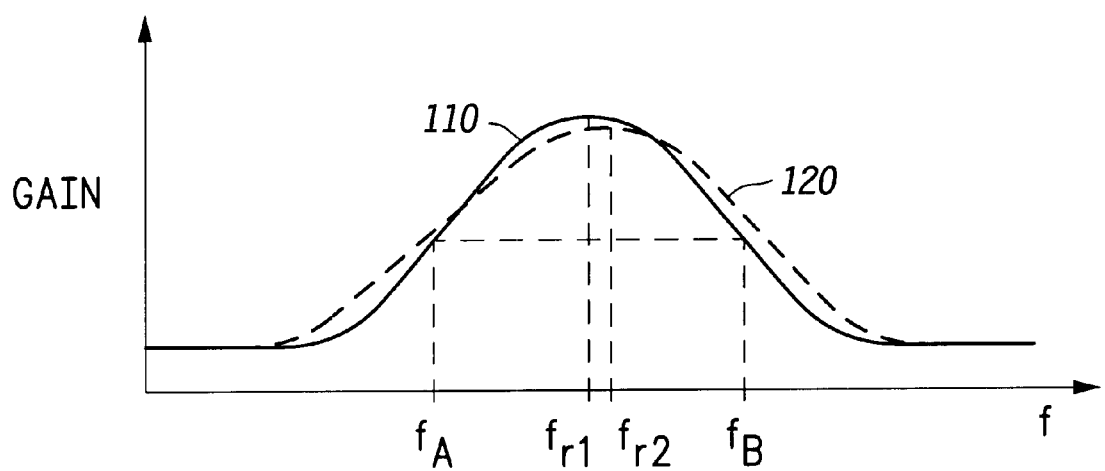
FIG. 3 illustrates a frequency graph associated with the determination of the resonant frequency of a membrane such that the stress of the membrane can be calculated in accordance with a particular embodiment of the present invention.

The invention can be better understood with reference to FIGS. 1–3. FIG. 1 illustrates a testing apparatus 10 that includes a piezoelectric plate 30 that excites or stimulates the membrane layer 50 of the mask 35. The mask 35 includes the membrane layer 50 and struts 40. The membrane layer 50 includes a plurality of membrane windows 52–56. The excitation of the membrane layer 50 of the mask 35 is measured using an optical sensing unit 90–98. The measurements taken by the optical sensing unit 90–98 are provided to a gain phase analyzer 80. The gain phase analyzer, which may be a Hewlett-Packard 4194A Gain Phase Analyzer, may also provide the excitation to the piezoelectric plate 30. Therefore, the gain phase analyzer 80 may include a spectrum analyzer and a signal generation circuit. By comparing the input signal provided to the piezoelectric plate 30 with the resulting excitation of the membrane window as detected by optical unit, the frequency response of the membrane window can be determined.

In order to isolate the remaining portions of the testing apparatus 10 from vibrations that may interfere with the performance of the measurements desired, a station 12 that isolates the rest of the testing apparatus 10 from external vibrations may be included. Upon the station 12, which functions as an isolation table, is a vacuum chamber 70 in which a chuck 20 is positioned. Because the chuck 20 does not play an active role in the excitation of the membrane layer 50, it can be a general purpose chuck and no customization is required to achieve the desired excitation of the membrane layer 50 as was required in prior art techniques that relied on electrostatic excitation.

A piezoelectric plate 30 is positioned on the chuck 20. The piezoelectric plate 30 may be a piezoelectric film, or other thin layer of piezoelectric material that vibrates in response to applied voltages. By controlling the frequency of the voltage applied to the piezoelectric plate 30, different frequencies of vibration can be achieved. Therefore, an electrical signal of varying frequency may be applied to the piezoelectric plate such that acoustic oscillation of varying frequency is applied to the membrane layer 50. The membrane layer 50 is supported by a plurality of struts 40, where the struts 40 may be positioned in a strut array, which may be referred to as "grillage."

The grillage supports the overlying membrane layer 50, which includes a plurality of membrane windows 52–56. The vibrations produced by the piezoelectric plate 30 are transferred through the struts 40 to the membrane layer 50. When the frequency of vibrations reaches the resonant frequency of a particular membrane window, the amplitude of vibration of the membrane window will increase significantly with respect to the amplitude of vibration in response to frequencies outside of the resonant frequency area. By performing this within a vacuum environment 70, the dampening effects associated with air molecules are minimized.

The vacuum environment 70 is enclosed by a transparent vacuum cover plate 60. In one embodiment, the vacuum cover plate is glass, where the thickness of the glass is sufficient to ensure maintenance of the vacuum environment 70. By providing a transparent vacuum cover plate 60, which may also be referred to as a view port, optical sensing techniques can be utilized to sense the frequency and amplitude of the vibrations of the membrane window 54 shown to be under test in FIG. 1. The frequency and amplitude of the vibrations of the membrane window 54 can be determined based on optical measurement techniques currently known in the art.

The optical measurement system shown in FIG. 1 includes a laser source 90 that generates a DC light source. This generated laser light is directed toward the membrane window under test using a fiber optic/collimation block 92 that directs and collimates the DC light source. As such, a collimated beam of light is directed at the membrane window 54 that is under test. Measurement of the vibrations of the membrane window under test may be enhanced by directing the beam of light toward the center portion of the membrane window under test. Because the center portion is the portion at which displacement of the membrane window 54 is most pronounced, maximum signal detection can be achieved.

Reflected light, which is actually a beam of light modulated by the membrane vibration, are received and collected by the fiber optic unit 96. The collected portions are provided to the photo detector/amplifier block 98. The photo detector/amplifier block 98, which acts as a light detector, converts the light into electrical signals (which may be referred to as a reflected signal) which are then amplified and provided to the gain phase analyzer 80. The analysis of the reflected signal can determine the frequency response of the vibrations of the membrane window 54 currently under test.

In order to allow the optical sensing system to be adjusted to target different membrane windows on the membrane mask 50, the fiber optic units 92 and 96 are preferably coupled via a base 94. As such, repositioning of the base 94 is all that is required to step from one membrane window to the next.

The gain phase analyzer 80 receives the electrical signals from the photo detector/amplifier 98. The gain phase analyzer 80 may also be the circuit that supplies the excitation voltage to the piezoelectric plate 30. As such, the gain phase analyzer 80 can normalize the electrical signals produced by the photo detector/amplifier 98 with those used to stimulate the piezoelectric plate 30 such that gain and phase information corresponding to the vibrations at the membrane window 54 under test can be determined based on frequency.

FIG. 3 illustrates a graph that shows the gain associated with the input and output signals in the testing apparatus 10. As is shown, the gain associated with different frequencies will vary for the membrane window 54 under test. The highest amount of gain for the curve 110 is realized at the resonant frequency of the membrane window 54, where this resonant frequency is indicated by the label $f_{r1}$. If a constant amplitude variable frequency electrical signal is applied to the piezoelectric plate, the resonant frequency is the frequency at which the vibration of the membrane window has the maximum amplitude. The resonance characteristics of the membrane window 54 can be determined based on two frequencies $f_A$ and $f_B$, which represent points on the frequency response curve 110 where the gain is one-half of the gain associated with the resonant frequency. The Q value associated with the membrane window 54 can be determined by dividing the resonant frequency by the difference in frequency between the frequency points $f_A$ and $f_B$.

FIG. 3 also illustrates a second curve 120, which is slightly distorted with respect to the curve 110. The curve 120 may represent a frequency response curve determined using prior art RFT techniques that require higher excitation voltages. These higher excitation voltages, both DC offset and AC signal voltages, may result in resonant frequency shifting, which is illustrated by the resonant frequency for the curve 120, $f_{r2}$. Furthermore, the general shape of the frequency curve may also be altered by the high voltages required for excitation in such prior art RFT systems. This is because the high voltages may force the vibrations outside of a linear vibration region, which is where true resonance intrinsic to the membrane window should be measured. As such, measurements achieved through these prior art techniques may not accurately represent the resonant frequency of the membrane window under test.

In order to achieve the desired frequency response, the gain phase analyzer 80 provides excitation to the piezoelectric plate 30 such that the frequency with which the piezoelectric plate 30 vibrates sweeps from a minimum frequency to a maximum frequency, where the expected resonant frequency is contained within the range defined by the minimum and maximum frequencies.

Note that in other embodiments, the piezoelectric plate excitation of the membrane layer 50 may be combined with capacitance based frequency and amplitude measurement techniques, such as those described above with respect to the prior art RFT technique. Thus, the excitation of the membrane layer 50 is achieved using the piezoelectric plate 30. However, rather than measuring the resulting vibrations using optical measurement devices, a sense electrode that detects changes in capacitance with respect to the vibrating membrane window is used. Note that in such embodiments, a conductive layer is required to be present within the membrane window such that the membrane window can be biased to allow the capacitive measurement to be performed using the sense electrode.

Although an embodiment that combines capacitance-based frequency and amplitude measurement techniques with piezoelectric excitation does suffer some limitations in that it requires a conductive layer within the membrane window, it does provide for a uniform chuck/piezoelectric plate combination that can be used for different membrane masks of different sizes and different configurations. As such, a new excitation apparatus that includes a number of customized drive electrodes situated to correspond to the locations of the membrane windows on the membrane mask does not have to be generated for each alteration in either the membrane mask size or configuration of membrane windows within the membrane mask.

In another embodiment, the optical measurement system described herein may be used to measure the vibrations of a membrane window that has been caused to vibrate by electrostatic excitation or through the application of another type of force that initiates vibration. Although this provides an advantage over prior art systems in that the noise coupling between the electrical stimulation and measurement of the membrane window is greatly reduced or eliminated, the inclusion of a conductive layer in the membrane mask is still required in order to permit electrostatic excitation of the membrane mask.

FIG. 2 illustrates an expanded view of the membrane window 54 under test in the testing apparatus as described with respect to FIG. 1 above. The membrane window 54 is shown to include a plurality of layers. Generally, SCALPEL masks are generated using a number of layers. The base layer may be a silicon nitride layer that is approximately 1,000 angstroms thick. Overlying the base layer 62 are scatterer layers 64 and 66. The scatterer layer 64 may be a chromium layer that is approximately 100 angstroms thick. The scatterer layer 66 may be a tantalum silicon nitride layer, or any other film material with an atomic number greater than 70, that is approximately 300 angstroms thick.

The scatterer layers 64 and 66 can be patterned at subsequent steps to allow for selective passage of an electron beam or other high-energy lithographic exposure tool. Thus, after patterning, portions of the membrane window which still include the scatterer layers will impede the penetration of the electron beam, thus allowing for patterning of the underlying substrate coated with photo sensitive materials.

Because the stress measurement technique described herein utilizes optical measurement techniques, there is no requirement that a conductive layer be included in the layers making up the membrane mask 50. For example, the stress associated with the base layer 62 alone can be measured even if the base layer 62 is an insulator, or generally non-conductive. Such stress measurement of the base layer presents a major challenge when using prior art RFT techniques, as when the base layer is formed of silicon nitride or silicon carbide, inadequate conduction is available to perform the electrostatic excitation or capacitive measurements required.

In other embodiments, different scatterer layer materials may be used that do not provide the conductivity associated with the chromium and tantalum silicon nitride layers commonly used in current SCALPEL masks. As such, the stress associated with the overall membrane mask may not be measured for such membranes unless an additional conductive layer is added. The addition of such a conductive layer may have detrimental effects in the form of added cost associated with the additional processing and also in the form of additive stress induced by the conductive layer.

Another advantage provided by the present stress measurement technique is realized in that patterned membrane masks can still be measured to determine their respective stress levels. This was not possible in prior art solutions, as patterning the membrane mask requires etching away of portions of the scatterer layers, which also serve as the conductive layers that allow for excitation and capacitive measurements to occur. This is not a problem when the excitation of the membrane mask is based on a mechanical or acoustical transference of vibration from the piezoelectric plate 30 to the membrane mask 35, as this does not require electrical conductivity within any layer of the membrane mask 35. Similarly, the measurement techniques that utilize optical sensing do not require any electrical conductivity within the membrane mask. As such, etching away portions of the scatterer layers does not affect either the excitation of the membrane mask nor the measurements associated with determining the frequency and amplitude of the vibrations induced in the membrane mask 35.

All of these advantages are realized without the need for specialized equipment that must be reconfigured to match any changes in the structure of the membrane mask 35. The ease with which the optical measurement system can be shifted from one membrane window to the next (without breaking the vacuum) allows the testing to be performed efficiently. Furthermore, the results produced by the gain phase analyzer allow for easy detection of the desired resonant frequency without the inaccuracies associated with determining the resonant frequency based on amplitude measurements that may be corrupted by noise. In addition, the accuracy of the measurements is enhanced due to the lower excitation voltages required to achieve the vibrations necessary to detect the resonant frequency. Although equipment which uses a laser light source, reflection of light, detection of light, and analysis to provide detection of vibration is believed to have advantages, there may also be other equipment which can provide the requisite vibration detection.

In the foregoing specification, the invention has been described with reference to specific embodiments. However, one of ordinary skill in the art appreciates that various modifications and changes can be made without departing from the scope of the present invention as set forth in the claims below. Accordingly, the specification and figures are to be regarded in an illustrative rather than a restrictive sense, and all such modifications are intended to be included within the scope of present invention.

Benefits, other advantages, and solutions to problems have been described above with regard to specific embodiments. However, the benefits, advantages, solutions to problems, and any element(s) that may cause any benefit, advantage, or solution to occur or become more pronounced are not to be construed as a critical, required, or essential feature or element of any or all the claims. As used herein, the terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus.

What is claimed is:

1. A method for detecting a resonant frequency of a membrane window of a membrane mask having struts which support the membrane window, comprising the steps of:
   providing a chuck;
   placing a piezoelectric plate on the chuck;
   placing the membrane mask on the piezoelectric plate;
   applying an electrical signal of a variable frequency to the piezoelectric plate to apply an acoustic oscillation to the membrane mask at the variable frequency;
   varying the variable frequency of the electrical signal;
   applying a laser light to the membrane window;
   receiving reflected light from the membrane window; and
   using the reflected light to determine the resonant frequency of the membrane window.

2. The method of claim 1, wherein prior to determining the resonant frequency of the membrane window, establishing a vacuum environment for the membrane mask on the piezoelectric plate.

3. The method of claim 2, wherein the membrane window has an amplitude and frequency of vibration in response to the electrical signal.

4. The method of claim 3, wherein the resonant frequency is determined by determining a frequency of vibration at which the amplitude of vibration is at a maximum.

5. The method of claim 4, wherein the membrane mask is a scattering with angular limited projection in electron-beam lithography (SCALPEL) mask.

6. A method for detecting a resonant frequency of a membrane window of a membrane mask having struts that support the membrane window, comprising the steps of:
   providing a chuck;
   placing a piezoelectric plate on the chuck;
   placing the membrane mask on the piezoelectric plate;
   applying an electrical signal of a variable frequency to the piezoelectric plate to apply an acoustic oscillation to the membrane window at the variable frequency; and
   detecting a vibration of the membrane window to determine the resonant frequency.

7. The method of claim 6, wherein the vibration of the membrane window has a frequency and an amplitude.

8. The method of claim 7, wherein the step of detecting the vibration of the membrane window further comprises detecting the frequency and the amplitude of the vibration of the membrane window.

9. The method of claim 8, wherein the step of detecting the vibration further comprising determining a frequency of vibration at which the amplitude of vibration is at a maximum.

10. The method of claim 9, wherein the membrane mask is a scattering with angular limited projection in electron-beam lithography (SCALPEL) mask.

11. The method of claim 10, wherein the membrane window includes silicon nitride, chromium, and a film of material with an atomic number greater than 70.

12. The method of claim 10, wherein the membrane window includes silicon nitride, chromium, and tantalum silicon nitride.

13. The method of claim 10, wherein the membrane window is an insulator.

14. The method of claim 10, wherein the step of detecting a vibration uses optical means.

15. The method of claim 14, wherein the optical means comprises a light source directed at the membrane window, a light detector directed at the membrane window, and a gain phase analyzer coupled to the light detector.

16. The method of claim 15, wherein the gain phase analyzer provides the electrical signal.

17. A method for detecting a resonant frequency of a membrane window of a membrane mask having struts that support the membrane window, comprising the steps of:
   applying a force to the membrane window to cause a vibration thereof;
   applying a laser light to the membrane window;
   receiving reflected light from the membrane window; and
   using the reflected light to detect an amplitude and frequency of the vibration of the membrane window and determine the resonant frequency of the membrane window.

18. The method of claim 17, wherein the step of using the reflected light further comprises determining the frequency of the vibration of the membrane which occurs at the maximum amplitude.

19. The method of claim 18 wherein the reflected light is converted to a reflected signal that is provided to a gain phase analyzer.

20. The method of claim 19, wherein the membrane window comprises silicon nitride, chromium, and tantalum silicon nitride.

21. The method of claim 19, wherein the membrane window comprises silicon nitride, chromium, and a film of material having an atomic number greater than 70.

22. The method of claim 19, wherein the membrane window is an insulator.

23. The method of claim 19, wherein the step of applying force to the membrane window further comprises:
   providing a chuck;
   placing a piezoelectric plate on the chuck;
   placing the membrane mask on the piezoelectric plate; and
   applying an electrical signal of a variable frequency to the piezoelectric plate to apply an acoustic oscillation to the membrane window at the variable frequency.

24. The method of claim 23, wherein the step of applying an electrical signal occurs in a vacuum environment.

25. An apparatus for detecting a resonant frequency of a membrane window of a membrane mask, comprising:
   a vacuum chamber having a chuck;
   a piezoelectric plate on the chuck for physically supporting the membrane mask and for receiving an electrical Wherein the electrical signal induces a vibration in the membrane window signal;
   a laser light source directed at the membrane window;
   a detector for receiving reflected light from the membrane window; and
   a spectrum analyzer coupled to the detector for determining the resonant frequency of the membrane.

26. The apparatus of claim 25 further comprising a vibration isolation table for supporting the chuck.

27. The apparatus of claim 26, further comprising a gain phase analyzer that includes the spectrum analyzer and generates the electrical signal.

28. An apparatus for detecting a resonant frequency of a membrane window of a membrane mask, comprising:
   a vacuum chamber having a chuck;
   a piezoelectric plate on the chuck for physically supporting the membrane mask and for receiving an electrical signal, wherein the electrical signal induces a vibration in the membrane window, the vibration having a frequency and an amplitude; and
   vibration detection means for detecting the amplitude and frequency of the vibration of the membrane to determine the resonant frequency.

29. The apparatus of claim 28, further comprising a vibration isolation table for supporting the chuck.

30. The apparatus of claim 29, wherein the membrane window is an insulator.

31. The apparatus of claim 30, wherein the membrane mask is a scattering with angular limited projection in electron-beam lithography (SCALPEL) mask.

32. An apparatus for detecting a resonant frequency of a membrane window of a membrane mask, comprising:
   means for inducing the membrane window to have a vibration, said vibration having a frequency and an amplitude;
   a laser light source directed at the membrane window;
   a detector for receiving reflected light from the membrane window; and
   a spectrum analyzer coupled to the detector for determining the resonant frequency of the membrane window.

33. The apparatus of claim 32, wherein the spectrum analyzer determines the resonant frequency of the membrane window by determining a frequency of vibration at which the amplitude is a maximum.

34. The apparatus of claim 33, further comprising an amplifier, wherein said amplifier couples the detector to the spectrum analyzer.

* * * * *

UNITED STATES PATENT AND TRADEMARK OFFICE
CERTIFICATE OF CORRECTION

PATENT NO. : 6,477,898 B1
DATED : November 12, 2002
INVENTOR(S) : Han et al.

It is certified that error appears in the above-identified patent and that said Letters Patent is hereby corrected as shown below:

Column 10,
Line 20, delete "signal".

Signed and Sealed this

Twelfth Day of August, 2003

JAMES E. ROGAN
*Director of the United States Patent and Trademark Office*